United States Patent
Priest et al.

(10) Patent No.: US 9,726,919 B2
(45) Date of Patent: Aug. 8, 2017

(54) WATER RESISTANT OPERATING ROOM DISPLAY

(71) Applicant: Black Diamond Video, Inc., Richmond, CA (US)

(72) Inventors: Edward Priest, Richmond, CA (US); Daniel H. Tomlinson, Jr., Duarte, CA (US)

(73) Assignee: BLACK DIAMOND VIDEO, INC., Richmond, CA (US)

( * ) Notice: Subject to any disclaimer, the term of this patent is extended or adjusted under 35 U.S.C. 154(b) by 302 days.

(21) Appl. No.: 14/488,194

(22) Filed: Sep. 16, 2014

(65) Prior Publication Data
US 2015/0077532 A1 Mar. 19, 2015

Related U.S. Application Data

(60) Provisional application No. 61/878,871, filed on Sep. 17, 2013.

(51) Int. Cl.
*H04N 5/64* (2006.01)
*G02F 1/1333* (2006.01)
*G06F 1/16* (2006.01)
*A61B 90/00* (2016.01)

(52) U.S. Cl.
CPC ...... *G02F 1/133308* (2013.01); *G06F 1/1601* (2013.01); *G06F 1/1626* (2013.01); *G06F 1/1637* (2013.01); *G06F 1/1656* (2013.01); *A61B 2090/372* (2016.02); *G02F 2001/133311* (2013.01); *G02F 2001/133328* (2013.01); *G02F 2201/50* (2013.01); *G06F 2200/1612* (2013.01)

(58) Field of Classification Search
None
See application file for complete search history.

(56) References Cited

U.S. PATENT DOCUMENTS

| | | | |
|---|---|---|---|
| 5,583,742 | A | 12/1996 | Noda et al. |
| 5,586,002 | A | 12/1996 | Notarianni |
| 5,844,772 | A | 12/1998 | Lee et al. |
| 6,132,367 | A | 10/2000 | Adair |
| 6,532,152 | B1 | 3/2003 | White et al. |
| 7,312,984 | B2 | 12/2007 | Richardson et al. |
| 7,495,895 | B2 | 2/2009 | Carnevali |

(Continued)

*Primary Examiner* — Christopher S Kelley
*Assistant Examiner* — Kaitlin A Retallick
(74) *Attorney, Agent, or Firm* — Loza & Loza, LLP; Razmig H. Messerian

(57) ABSTRACT

One feature pertains to a display monitor that includes a display having a front side surface that displays images and a frame housing the display. The frame includes at least one perimeter edge surface that extends along a perimeter of the display. The monitor further includes a protective rubber overmolding that removeably couples to and encases the perimeter edge surface. The frame may also include a front side surface that extends about a perimeter of the frame and is orthogonal to the perimeter edge surface, and the protective overmolding removeably couples to and encases the front side surface of the frame. A space may be present about the perimeter of the display between the frame's front side surface and the display's front side surface, and the protective overmolding includes a lip that resides within the space to form a liquid-resistant seal between the display and the frame.

16 Claims, 15 Drawing Sheets

(56) References Cited

U.S. PATENT DOCUMENTS

| | | |
|---|---|---|
| 7,733,642 B2 | 6/2010 | Liou et al. |
| 8,373,980 B2 | 2/2013 | Reber |
| 8,418,387 B2 | 4/2013 | Swatt et al. |
| 2006/0286868 A1* | 12/2006 | Pentell ............... H01H 85/2015 439/620.27 |
| 2009/0103001 A1* | 4/2009 | Choi ................. G02F 1/133308 349/58 |
| 2009/0256796 A1 | 10/2009 | Jang et al. |
| 2010/0149455 A1* | 6/2010 | Tsubokura ........ G02F 1/133308 349/58 |
| 2010/0171889 A1 | 7/2010 | Pantel et al. |
| 2011/0216482 A1* | 9/2011 | Moscovitch .......... G06F 1/1601 361/679.01 |
| 2012/0051022 A1 | 3/2012 | Dong et al. |
| 2012/0099266 A1 | 4/2012 | Reber et al. |
| 2013/0003273 A1 | 1/2013 | Takechi |
| 2013/0021731 A1* | 1/2013 | Wu ....................... G06F 1/1637 361/679.01 |
| 2013/0027862 A1 | 1/2013 | Rayner |
| 2014/0152890 A1* | 6/2014 | Rayner ................. G06F 1/1626 348/376 |

* cited by examiner

WATER RESISTANT OPERATING ROOM DISPLAY

CROSS-REFERENCE TO RELATED APPLICATIONS

The present application for patent claims priority to provisional application No. 61/878,871 entitled "Water-resistant Operating Room Display" filed Sep. 17, 2013, the entire disclosure of which is hereby expressly incorporated by reference.

BACKGROUND

Field

Various features relate to display monitors, and in particular, to liquid-resistant display monitors featuring a protective overmolding.

Background

Modern operating rooms feature technologically advanced equipment, such as computers, displays, advanced lighting systems, and other electronic equipment. For example, display monitors are now routinely used in operating rooms to assist doctors and other medical staff in performing many medical procedures including surgery. Such display monitors may be used, for instance, to display images received from a camera within a patient's body.

Given the type of environment such display monitors reside in, they are routinely exposed to fluids, moisture, microorganisms, and are also liable to receive ample physical wear. For example, such a display monitor is often attached to a boom arm that allows the display monitor to swivel above a patient and close to the medical staff performing and assisting with the medical procedure/surgery. In such a case, fluids such as blood, water, etc. find their way onto the display monitor given the monitor's close proximity to the patient and staff Moreover, the close proximity of these boom arm-supported display monitors to medical staff presents a subtle danger of accidental bodily harm to the staff. For example, it is not uncommon for surgeons and assisting medical staff to accidentally bump their heads against unseen display monitors that are suspended in air by the boom arms. The harm may be amplified given that display monitors typically have sharp corners and edges that make such accidents anything but trivial.

As mentioned above, modern operating rooms include and utilize a multitude of electronic devices. In many cases it would be advantageous if some of these electronic devices could directly interface with the display monitor. For example, it would be advantageous if peripheral devices such as video cameras, microphones, speakers, and/or wireless communication devices could couple to and directly interface with the display monitor, especially in a manner that secured the interface connections in a liquid-resistant fashion.

Thus, there exists a need for display monitors that are resistant to fluids, provide user safety against accidental contact, and also allow for a plurality of peripheral device connections.

SUMMARY

One feature provides a display monitor comprising a display having a front side surface that, at least a portion of, displays images, a frame housing the display, the frame including at least one perimeter edge surface that extends along an entire perimeter of the display, and a protective overmolding that removeably couples to and encases the perimeter edge surface, the overmolding being at least one of an elastic material, rubber, or silicone. According to one embodiment, the frame further includes a front side surface that extends about a perimeter of the frame and is substantially orthogonal to the perimeter edge surface, and the protective overmolding removeably couples to and encases the front side surface of the frame. According to another embodiment, the display monitor further comprises a space about the perimeter of the display between the front side surface of the frame and the front side surface of the display, and wherein the protective overmolding includes a lip that extends about the perimeter of the frame and resides within the space to form a liquid-resistant seal between the front side surfaces of the display and the frame. The lip is merely one example of a means for sealing the space that extends about the perimeter of the frame.

According to one embodiment, the frame further includes a back side surface that extends about the perimeter of the frame and is substantially orthogonal to the perimeter edge surface, and the protective overmolding removeably couples to and encases at least a portion of the back side surface of the frame. According to another embodiment, the back side surface includes a groove that extends about the perimeter of the frame, and the protective overmolding removeably couples to and encases the groove. According to yet another embodiment, the groove includes a well and the overmolding includes a notch that couples to and resides within the well.

According to one embodiment, the perimeter edge surface includes a first perimeter edge surface, a second perimeter edge surface, a third perimeter edge surface, and a fourth perimeter edge surface, the first and third perimeter edge surfaces parallel to each other, the second and fourth perimeter edge surfaces parallel to each other, and the first and third perimeter edge surfaces orthogonal to the second and fourth perimeter edge surfaces. According to another embodiment, a thickness of the third perimeter edge surface is at least 50% thicker than thicknesses of each of the first, second, and fourth perimeter edge surfaces. According to yet another embodiment, the frame further includes a back side surface having at least one peripheral device interface connection port, the interface connection port including an interface connector.

According to one embodiment, the interface connection port further includes an interface connector cover removeably coupled to the back side surface of the frame and configured to cover the interface connector, the interface connector cover further configured to prevent moisture from entering at least one of an interior cavity of the display monitor or the interface connector. According to another embodiment, the back side surface of the frame further has at least one access panel configured to allow access to an interior cavity of the display monitor, the access panel removeably coupled to the back side surface of the frame. According to yet another embodiment, the access panel includes fins and is configured to dissipate heat generated by the display monitor.

Another feature provides a display monitor comprising means for displaying images having a front side surface, means for housing the means for displaying images, the means for housing including at least one perimeter edge surface that extends about a perimeter of the means for housing, and means for protecting the display monitor, the means for protecting coupling to and encasing the perimeter edge surface and including at least one of an elastic material, rubber, or silicone. According to one embodiment, the means for housing further includes a front side surface that extends about the perimeter of the means for housing and is substantially orthogonal to the perimeter edge surface, and the means for protecting removeably couples to and encases the front side surface of the means for housing. According to another embodiment, the display monitor further comprises a space about the perimeter of the means for displaying images between the front side surface of the means for housing and the front side surface of the means for displaying images, and wherein the means for protecting includes a means for sealing the space that extends about the perimeter of the means for housing and resides within the space to form a liquid-resistant seal between the front side surfaces of the means for displaying and the means for housing.

According to one embodiment, the means for housing further includes a back side surface that extends about the perimeter of the means for housing and is substantially orthogonal to the perimeter edge surface, and the means for protecting removeably couples to and encases at least a portion of the back side surface of the means for housing. According to another embodiment, the back side surface includes a well that extends about the perimeter of the means for housing and the means for protecting includes a notch that couples to and resides within the well. According to yet another, the means for housing further includes a back side surface having at least one peripheral device interface connection port, the interface connection port including an interface connector and an interface connector cover removeably coupled to the back side surface of the frame, the interface connector cover configured to cover the interface connector and prevent moisture from entering at least one of an interior cavity of the display monitor or the interface connector.

Another feature provides a display monitor comprising a display having a front side surface that, at least a portion of, displays images, a frame housing the display, the frame including at least four perimeter edge surfaces that extend along a perimeter of the frame, and a rubber overmolding that couples to the perimeter edge surfaces and extends about the perimeter of the frame, the rubber overmolding including a means for sealing that resides within a space between the front side surface of the display and the frame and the means for sealing is configured to prevent liquid from entering an internal cavity of the display monitor through the space. According to one embodiment, the frame further includes a front side surface, the rubber overmolding further coupling to the front side surface of the frame, and the means for sealing resides within the space between the front side surface of the display and the front side surface of the frame.

BRIEF DESCRIPTION OF DRAWINGS

FIG. 1 illustrates the display monitor with a portion of the display monitor's overmolding removed to show a frame underneath. FIG. 2 illustrates the display monitor with the entire overmolding in place. FIG. 3 illustrates the display monitor with the overmolding removed.

FIG. 4 illustrates the display monitor with a portion of the overmolding removed. FIG. 5 illustrates the display monitor with the entire overmolding in place. FIG. 6 illustrates the display monitor with the overmolding removed.

DETAILED DESCRIPTION

In the following description numerous specific details may be set forth in order to provide a thorough understanding of the invention. However, one skilled in the art would recognize that the invention might be practiced without these specific details. In other instances, well known methods, procedures, and/or components have not been described in detail so as not to unnecessarily obscure aspects of the invention.

Figure 1:
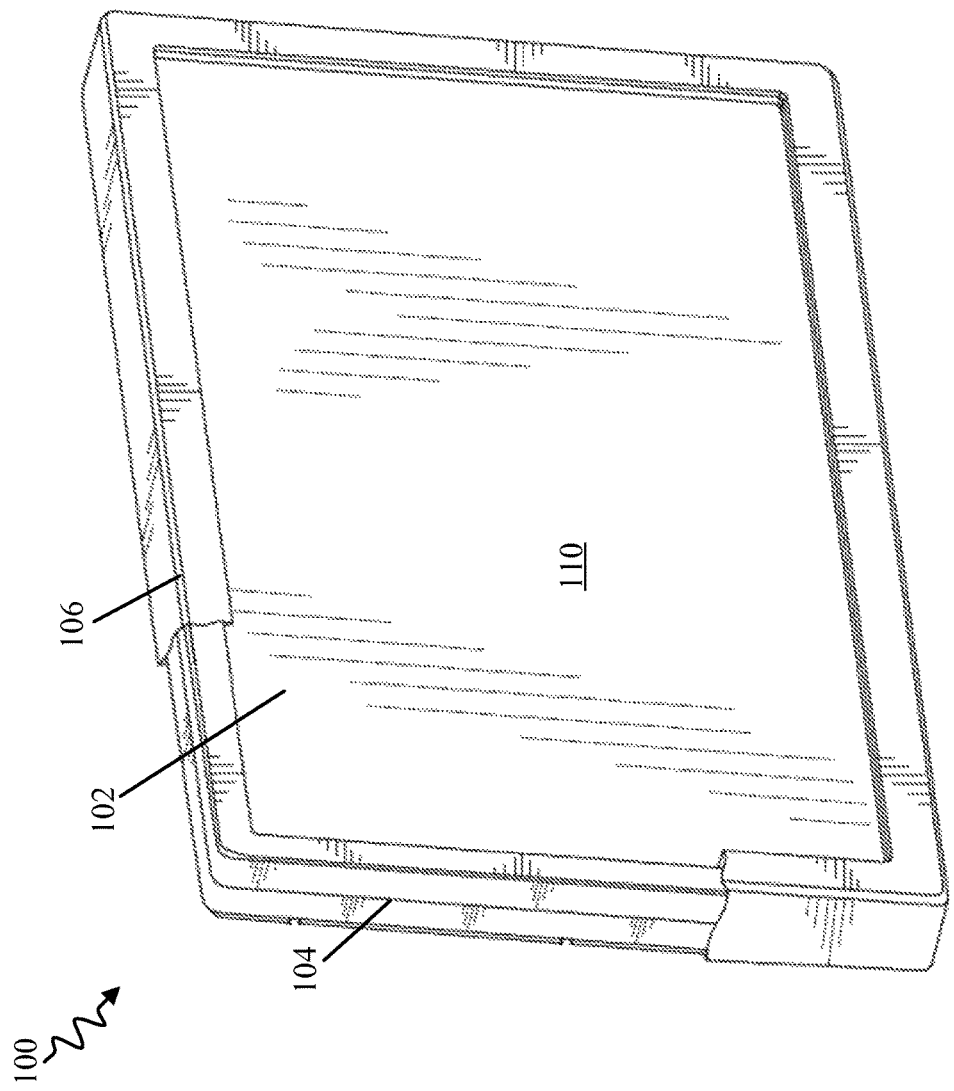
FIGS. 1, 2, and 3 illustrate front perspective views of a display monitor that may be used in any medical services setting such as an operating room.
Figure 2:
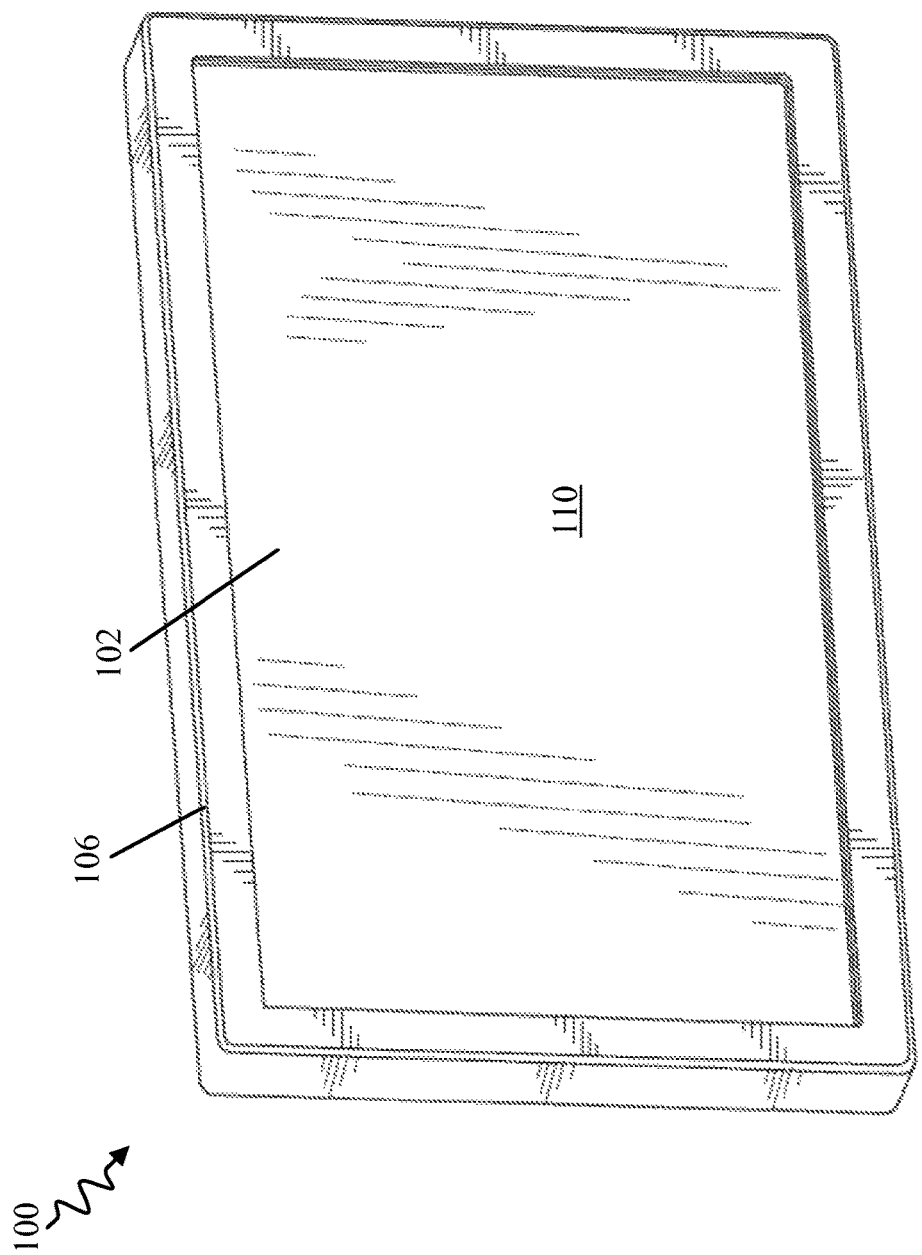
Figure 3:
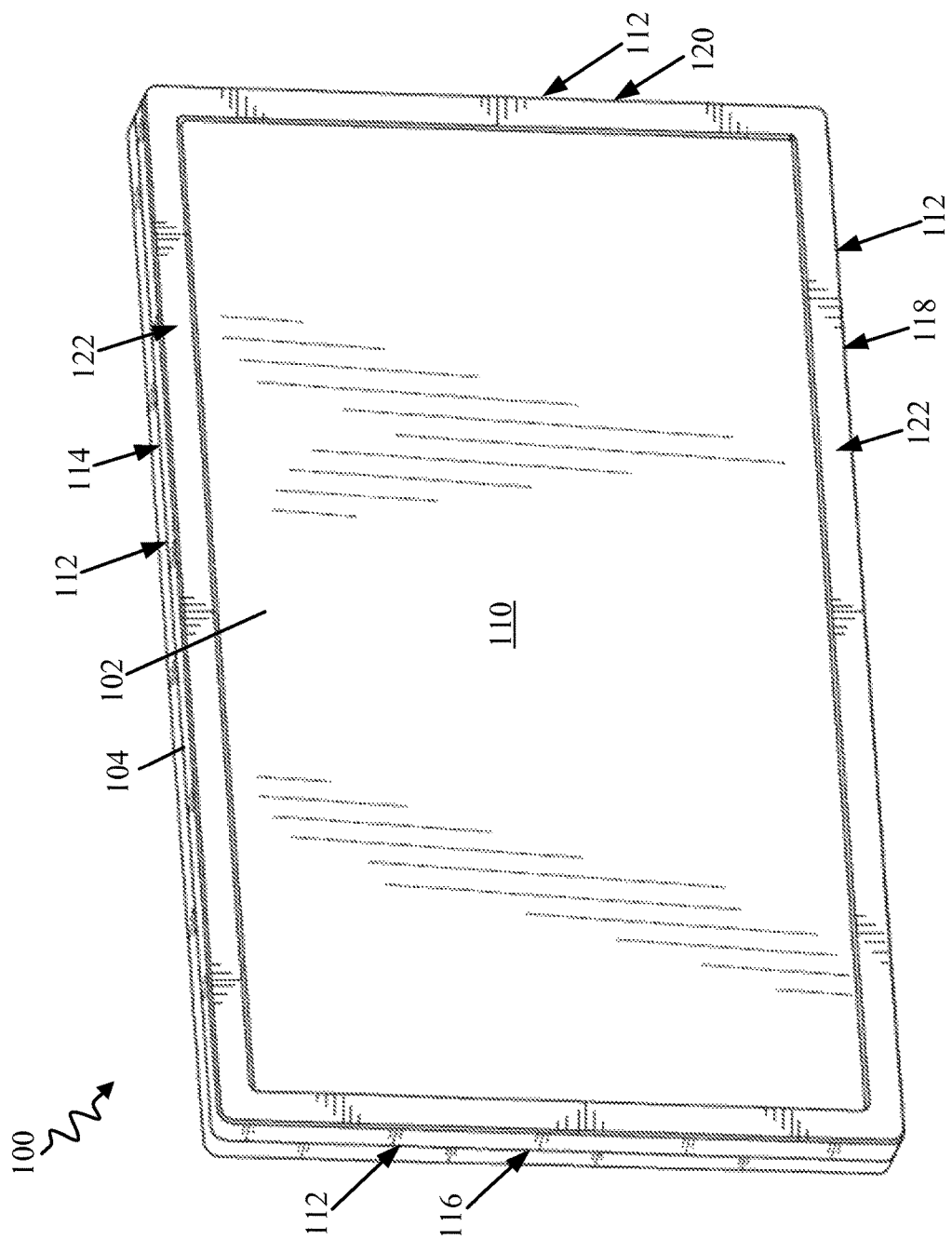

FIGS. 1, 2, and 3 illustrate front perspective views of a novel display monitor 100 according to one embodiment that may be used in any medical services setting such as an operating room. The display monitor 100 includes a display 102, a frame 104, and the protective overmolding 106. In FIG. 1 a portion of the overmolding 106 is removed to show the frame 104 underneath. FIG. 2 illustrates the monitor 100 with the entire overmolding 106, and FIG. 3 illustrates the monitor 100 with the overmolding 106 removed.

Referring to FIGS. 1 and 2, the display 102 (e.g., means for displaying images) may be any electronic display device such as, but not limited to, a plasma display device, a liquid crystal display (LCD) device, a flat panel technology display, a cathode ray tube (CRT) display device, etc. The display 102 includes a front side surface 110 that at least a portion of is configured to display images. When used in a medical services setting the display 102 will typically display images associated with patient care such as live surgical camera feeds, patient charts, previously acquired and stored medical images, etc.

Referring to FIG. 3, the frame 104 (e.g., means for housing the display) is a structural element of the display monitor 100 that houses the display 102. The frame 104 includes at least one perimeter edge surface 112 that extends along the entire perimeter of the display monitor 100 and/or display 102. In the example shown the perimeter edge surface 112 has a rectangular shape and is comprised of a first side perimeter edge surface 114, a second side perimeter edge surface 116, a third side perimeter edge surface 118, and a fourth side perimeter edge surface 120. The first and third side perimeter edge surfaces 114, 118 are parallel to each other and the second and fourth side perimeter edge surfaces 116, 120 are also parallel to each other. The first and third side perimeter edge surfaces 114, 118 are orthogonal to the second and fourth side perimeter edge surfaces 116, 120. According to different embodiments, the perimeter edge surface 112 is not rectangular but may be any other shape including, but not limited to, circular, oval, triangular, or have more than four sides. The frame 104 may further include a front side surface 122 that extends about the perimeter of the frame 104 and is substantially orthogonal to the perimeter edge surface 112.

Figure 4:
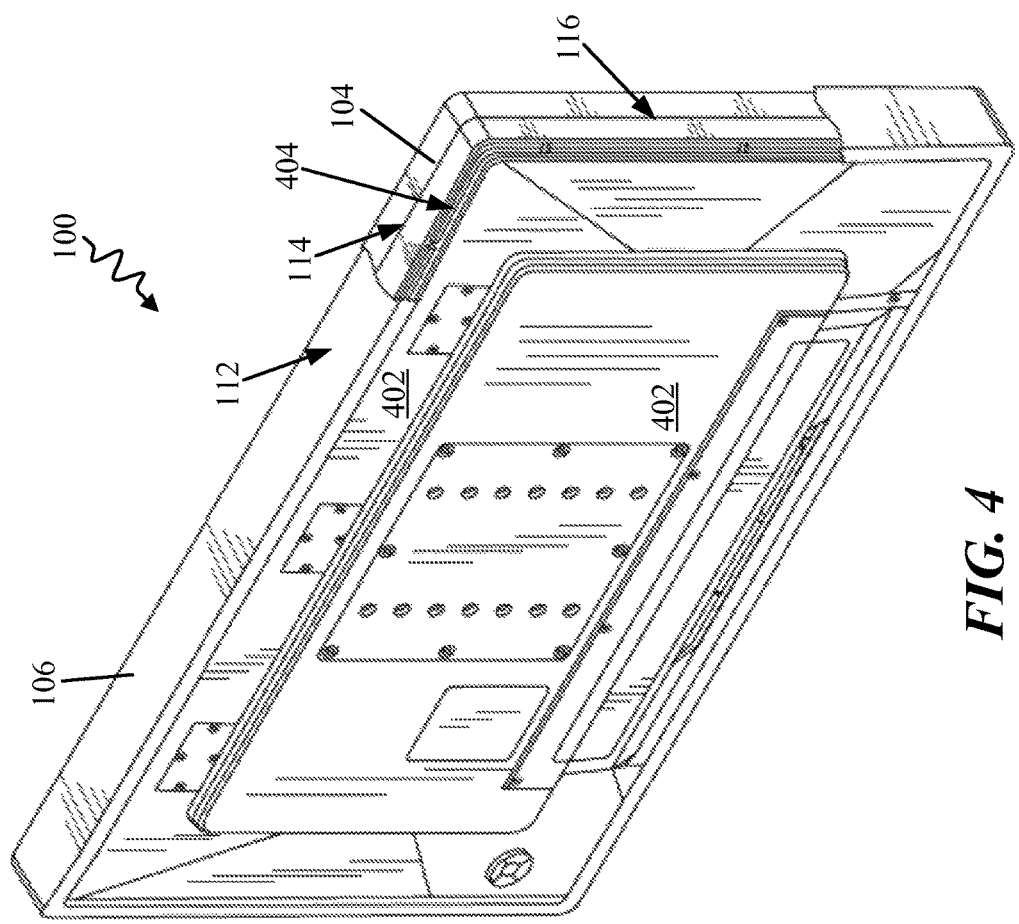
FIGS. 4, 5, and 6 illustrate rear perspective views of the display monitor.
Figure 5:
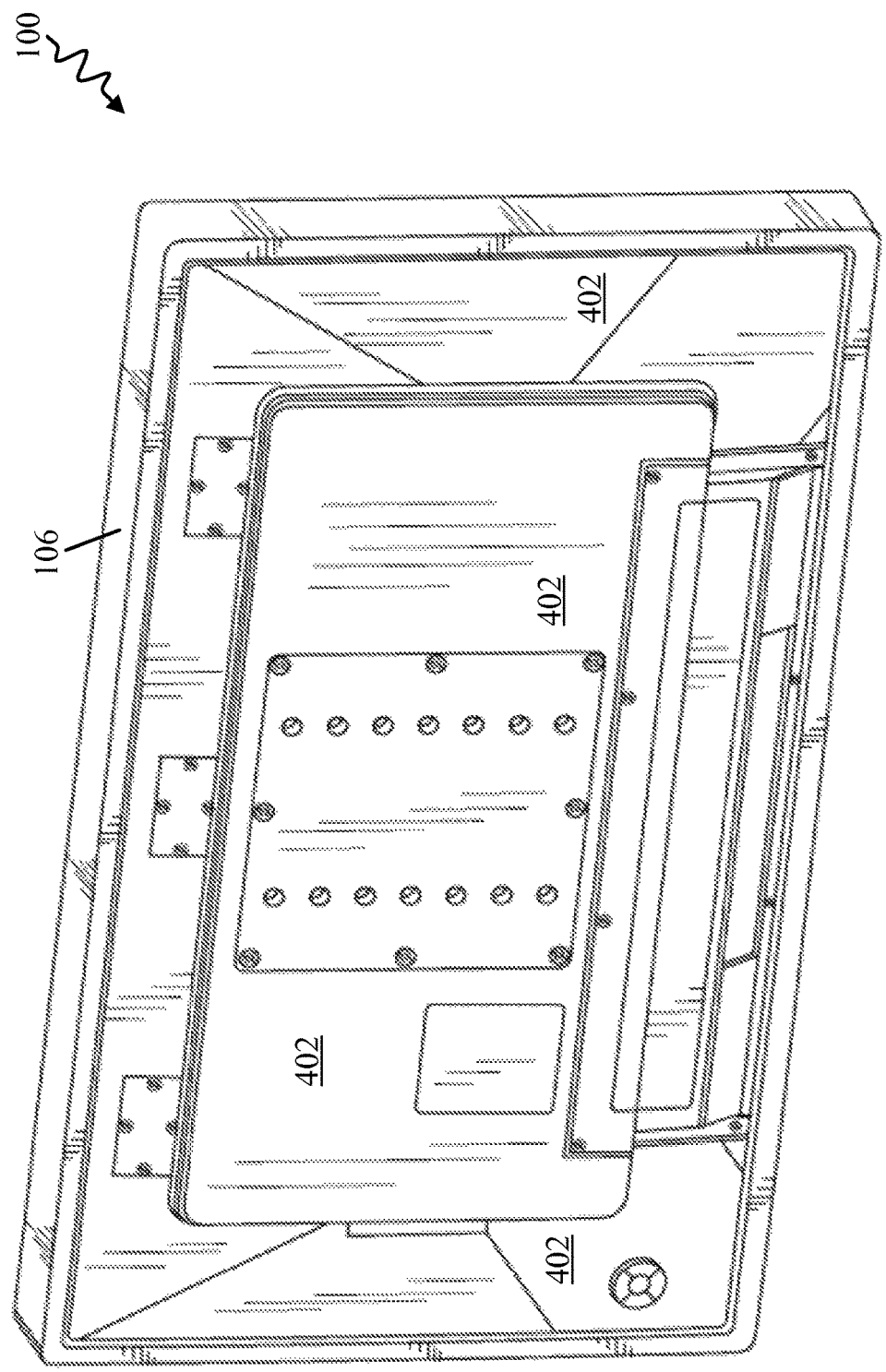
Figure 6:
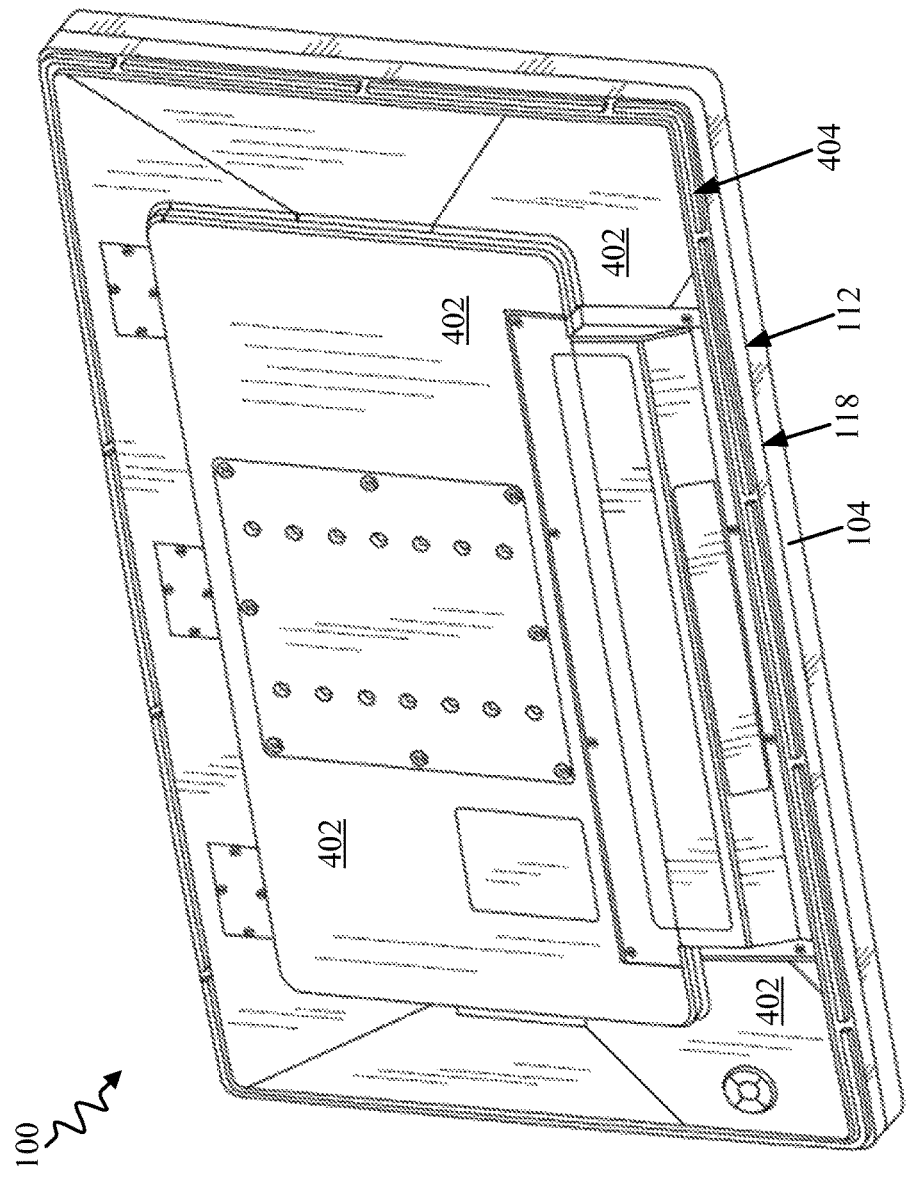

FIGS. 4, 5, and 6 illustrate rear perspective views of the display monitor 100 according to one embodiment. Specifically, FIG. 4 illustrates the monitor 100 with a portion of the overmolding removed. FIG. 5 illustrates the monitor 100 with the entire overmolding 106, and FIG. 6 illustrates the monitor 100 with the overmolding 106 removed. Referring to FIGS. 4-6, the frame 104 further includes a back side surface 402 that is substantially orthogonal to the perimeter edge surface 112. The back side surface 402 may include a groove 404 (e.g., back side groove) that extends about the perimeter of the frame 104.

The protective overmolding 106 may be composed of an elastic material, rubber, thermoplastic rubber (TPR), thermoplastic elastomer, and/or silicone. The overmolding 106 fits over the frame 104 and removeably couples to it. Specifically, the overmolding 106 removeably couples to and encases the perimeter edge surface 112 of the frame 104. In some embodiments, the overmolding 106 is permanently coupled to and/or may not be easily removed from the frame 104. The overmolding 106 (e.g., means for protecting the display monitor) is designed to absorb impacts to protect both the display monitor 100 from physical damage and also protect an operator from injury resulting from accidental collisions with the display monitor 100. Since medical service settings, such as operating rooms, can be crowded and cramped, collisions between personnel and equipment routinely occur. For example, the overmolding 106 may help protect a person's head from accidental contact with the display monitor 100 in cases where the monitor 100 is elevated and coupled to a boom arm. In one embodiment, an adhesive may be applied to the frame 104 and/or the underside of the overmolding 106 when placing the overmolding 106 over the frame 104 to better secure the overmolding 106 to the frame 104.

Figure 7:
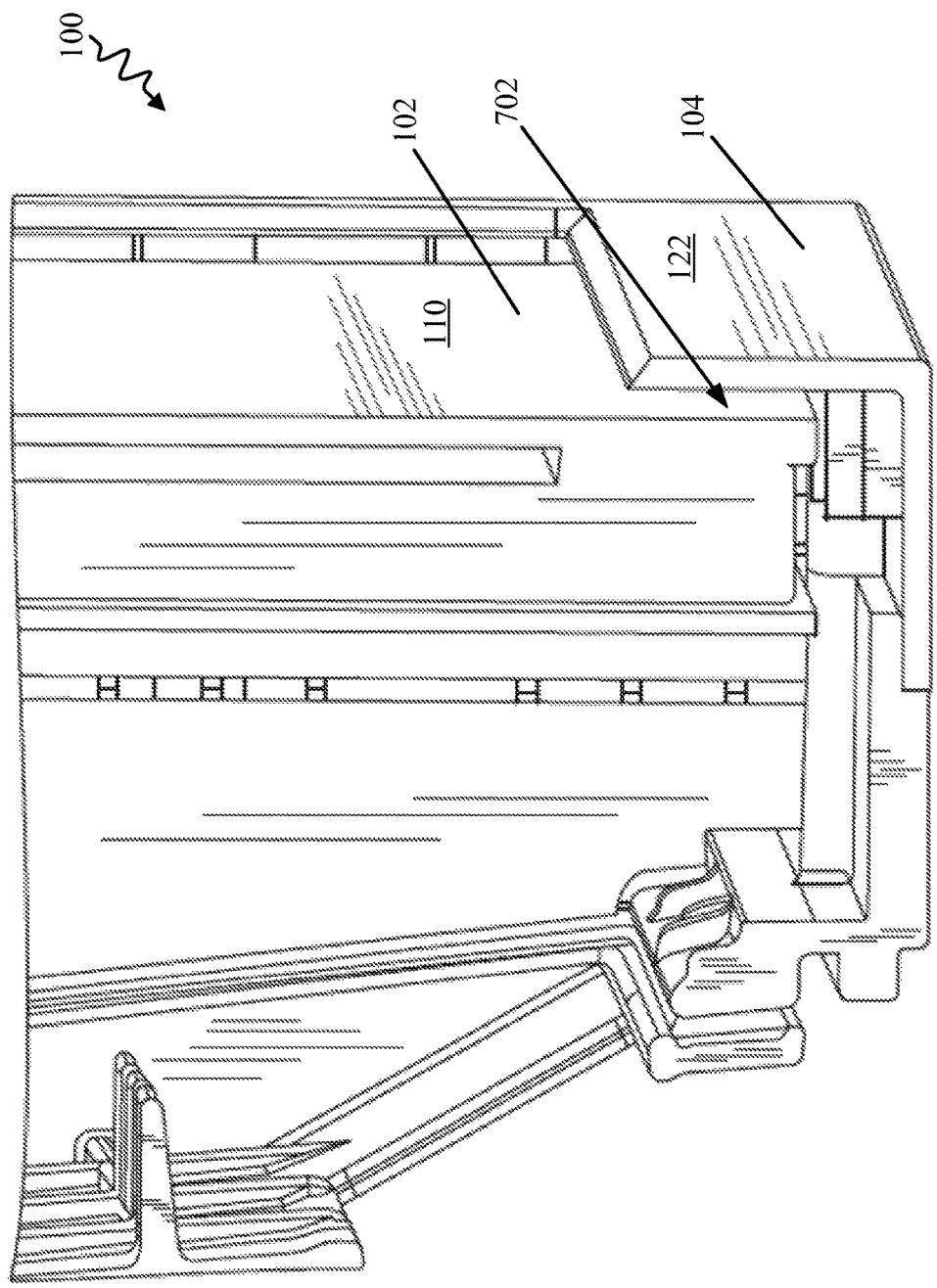
FIG. 7 illustrates a front perspective, cross-sectional view of a portion of the display monitor without the overmolding.
Figure 8:
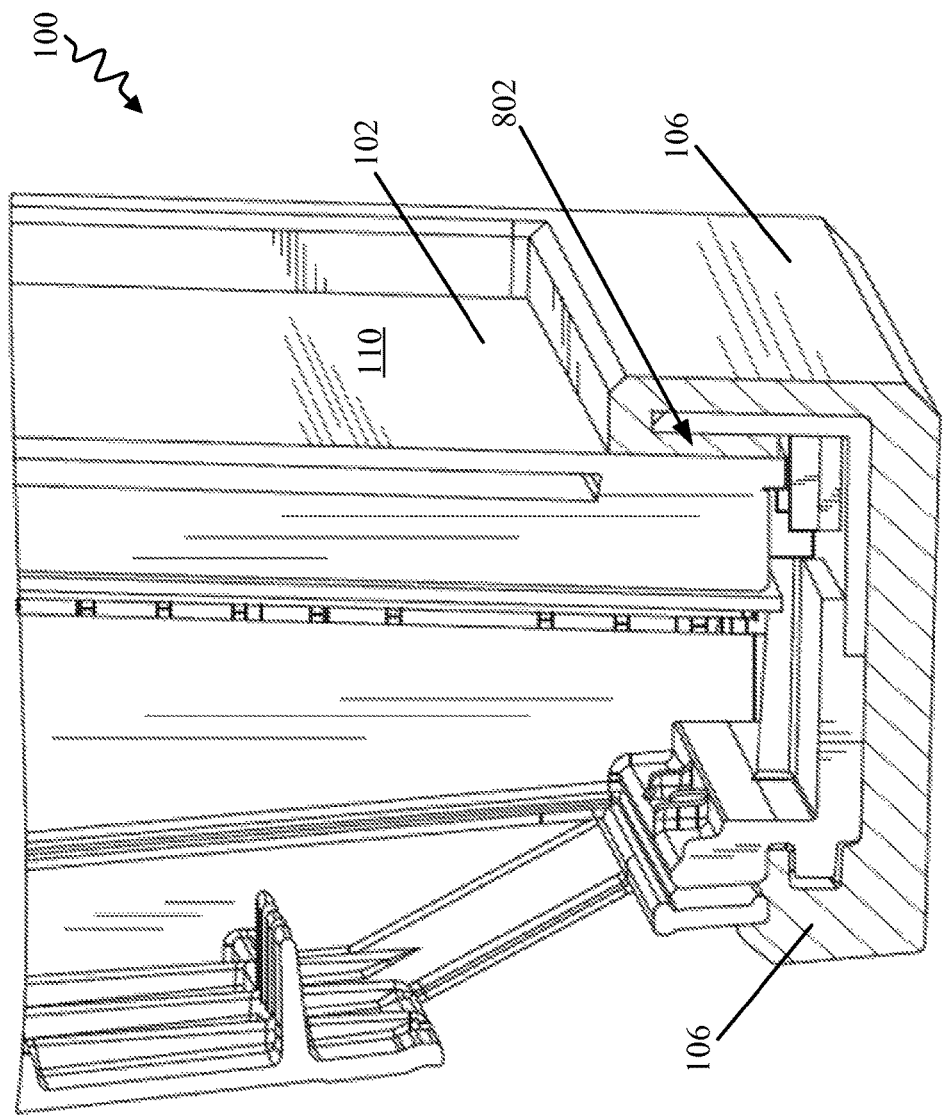
FIG. 8 illustrates a front perspective, cross-sectional view of the portion of the display monitor with the overmolding in place.

As shown in FIG. 2, the overmolding 106 may also couple to and encase the front side surface 122 of the frame 104. FIGS. 7 and 8 illustrate front perspective, cross-sectional views of a portion of the display monitor 100 according to one embodiment. Specifically, FIG. 7 illustrates the cross-section of the monitor 100 without the overmolding 106 in place and FIG. 8 illustrates the cross-section of the monitor 100 with the overmolding 106 secured in place. Referring to FIG. 7, a space 702 is formed between the front side surface 122 of the frame 104 and the front side surface 110 of the display 102. The space 702 may extend about the entire perimeter of the front side surface 104 of the frame 104.

Referring to FIG. 8, the overmolding 106 includes a lip 802 (e.g., may also be referred to herein as a "projection") that may also extend about the perimeter of the frame 104 and resides within the space 702. The lip 802 may be composed of the same type of material as the rest of the overmolding 106, namely a rubber, silicone, and/or other elastic and waterproof material.

Once the overmolding 106 is secured to the frame 104 by positioning the lip 802 within the space 702, a liquid-resistant seal is formed between the front side surfaces 110, 122 of the display 102 and frame 104. The seal (e.g., gasket seal) prevents liquids, such as water, blood, or other fluids, from entering the inside of the monitor 100 where moisture-sensitive circuitry may be found.

Figure 9:
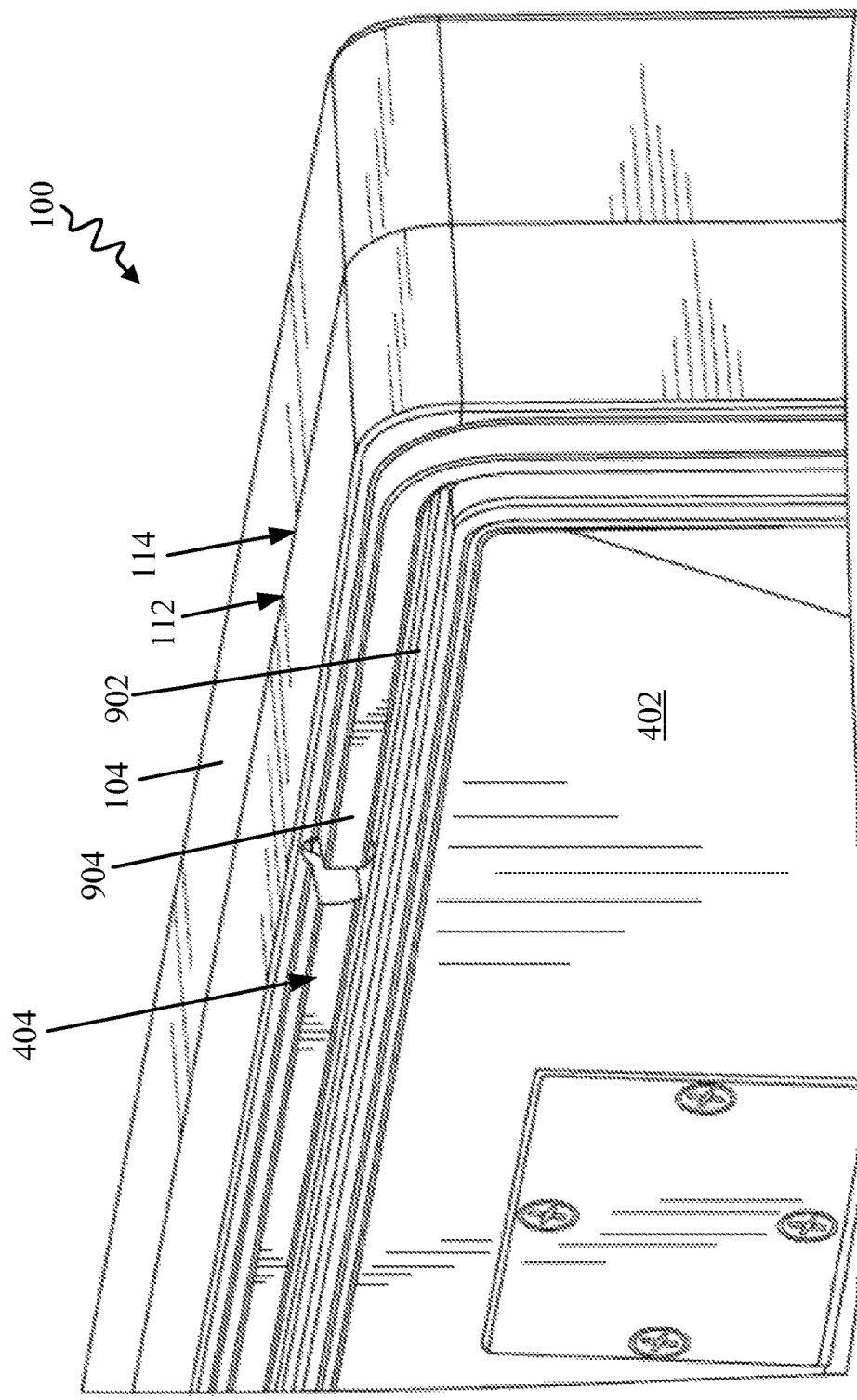
FIG. 9 illustrates a closer view of a groove of the display monitor.

Referring to FIG. 4, the overmolding 106 may also couple to and encase a portion of the back side surface 402 of the frame 104. For example, the overmolding 106 may couple to and encase the groove 404 of the back side surface 404 near the perimeter of the frame 104. FIG. 9 illustrates a closer view of the groove 404 according to one embodiment. The groove 404 may include a well 902 and a raised projection 904 (also may be referred to herein as "track"). The well 902 and track 904 help secure a corresponding portion of the overmolding 106 that matches the shape of the well 904 and track 906 to the frame 104.

The thickness of the overmolding 106 (i.e., the amount of overmolding covering the frame 104) may vary across different portions of the frame 104 depending on the portion of the frame 104 the overmolding 106 is covering. For example, referring to FIG. 3, the thickness of the overmolding 106 at the first perimeter edge surface 114, second perimeter edge surface 116, and fourth perimeter edge surface 120 may be less than the thickness of the overmolding 106 covering the third perimeter edge surface 118 (i.e., bottom of display monitor 100) since the latter surface may be more likely to be bumped into (e.g., if monitor 100 is suspended from a boom arm) it can be made thicker than the other portions of the overmolding 106. As just one non-limiting example, the portion of the overmolding 106 on the bottom side of the display monitor 100 (e.g., third perimeter edge surface 118) may be about 10% to 300% thicker than other portions of the overmolding 106. In one instance, the overmolding 106 at the third perimeter edge surface 118 may have a thickness of about 0.5 inch whereas the rest of the overmolding is about 0.25 inch thick.

Figure 10:
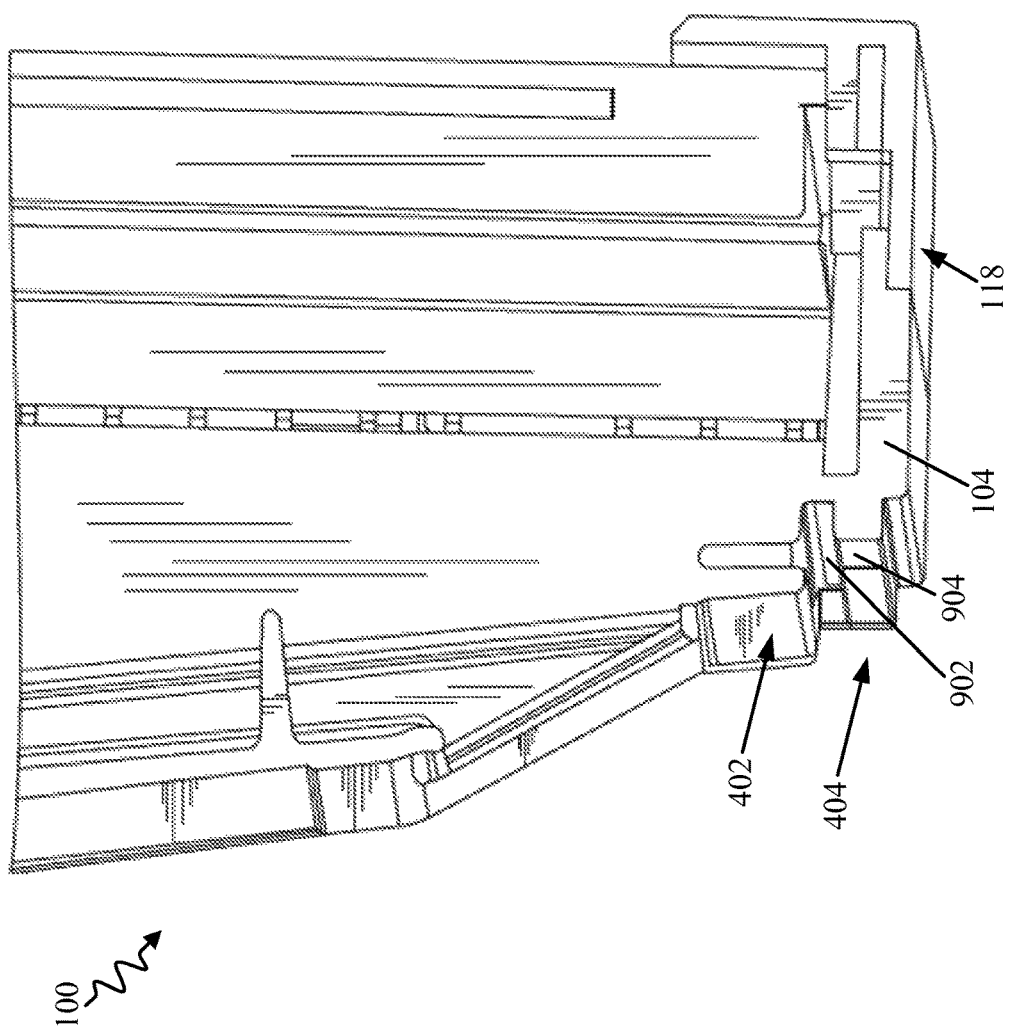
FIG. 10 illustrates a rear perspective, cross-sectional view of a portion of the display monitor without the overmolding.
Figure 11:
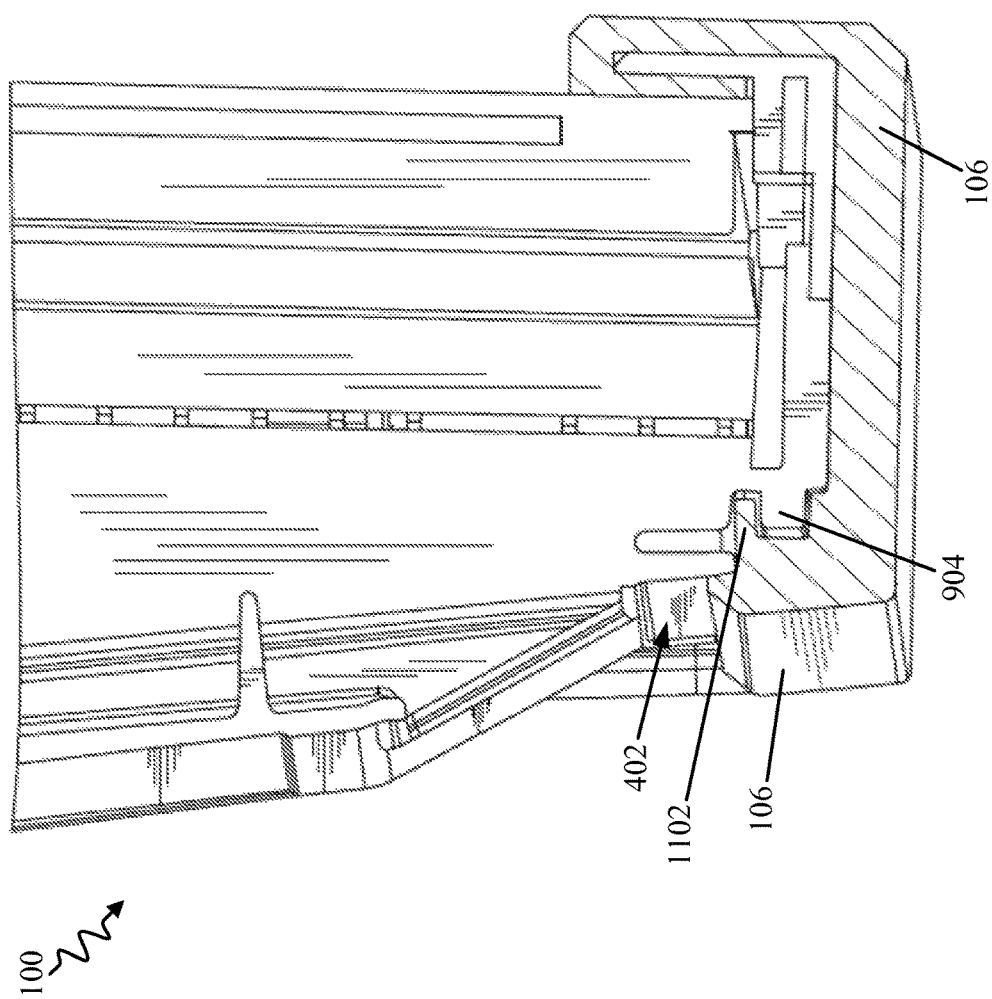
FIG. 11 illustrates a rear perspective, cross-sectional view of a portion of the display monitor with the overmolding in place.

FIGS. 10 and 11 illustrate rear perspective, cross-sectional views of a portion of the display monitor 100 according to one embodiment. Specifically, FIG. 10 illustrates the cross-section of the monitor 100 without the overmolding 106, and FIG. 11 illustrates the cross-section of the monitor 100 with the overmolding 106 secured in place. Referring to FIG. 11, the overmolding 106 may include a notch 1102 that fits and resides within the well 902. An adhesive material may be applied to the notch 1102, the well 902, and/or the track 904 to help secure the overmolding 106 to the frame 104. The notch 1102 may extend about the perimeter of the frame 104 and/or the overmolding 106.

In this fashion, the protective overmolding 106, including the seal formed by the lip 802 within the space 702, make the monitor 100 liquid and splash resistant. For example, the overmolding 106 allows the display monitor 100 to be easily cleaned with cleaning fluids such as solvents, detergents, antibacterial washes, etc. without fear of damaging water-sensitive electronic components within the monitor 100.

Figure 12:
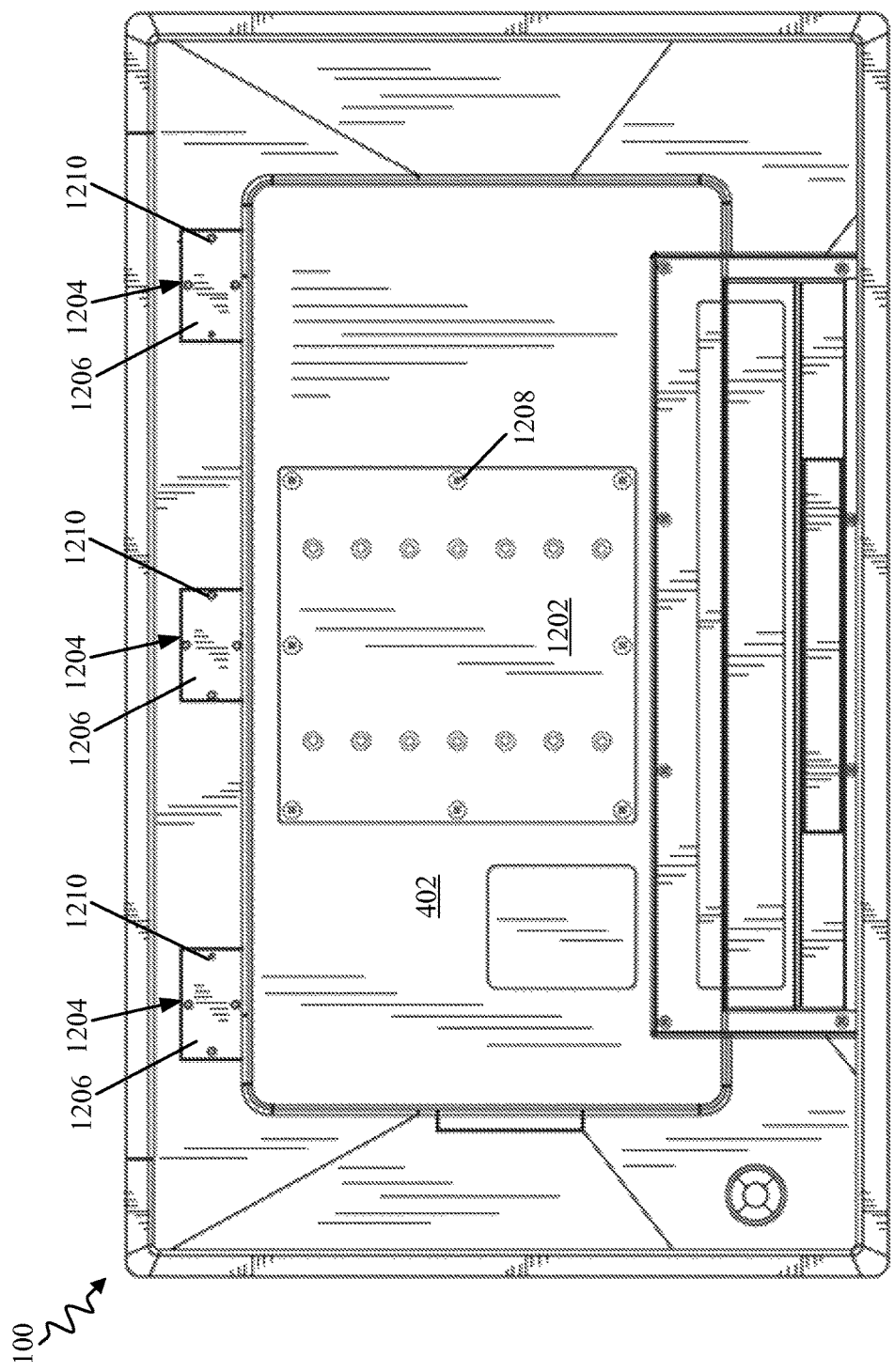
FIG. 12 illustrates a rear view of the display monitor.
Figure 13:
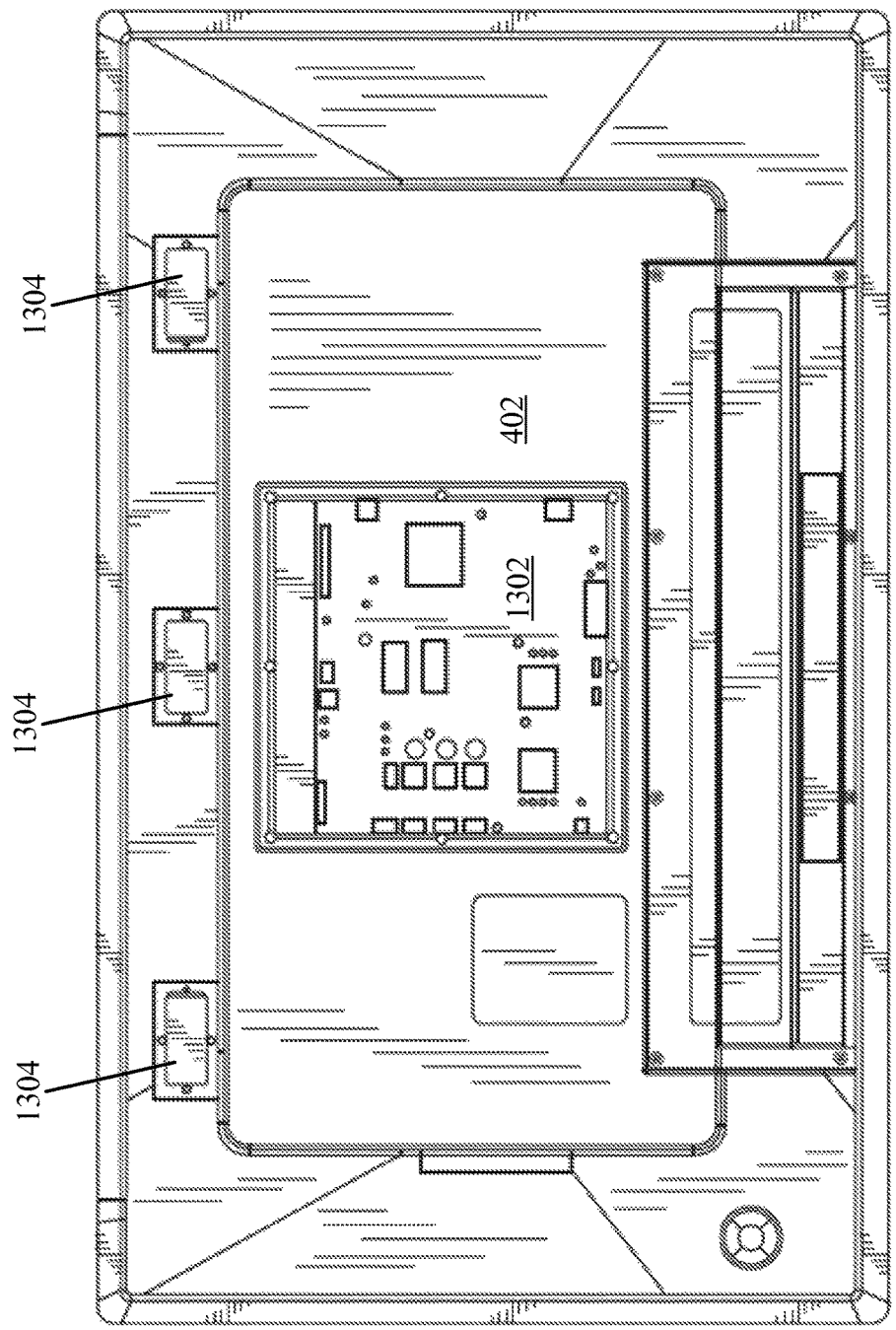
FIG. 13 illustrates a rear view of the display monitor with an access panel and interface connector covers removed.

FIGS. 12 and 13 illustrate rear views of the monitor 100 according to one embodiment. In the example shown, the monitor's 100 frame 104 (e.g., the back side surface 402) may include an access panel 1202 and one or more peripheral device interface connection ports 1204. The interface connection ports 1204 may each include an interface connector cover 1206. FIG. 13 shows the monitor 100 with the access panel 1202 and the interface connector covers 1206 removed. In the example shown, the monitor 100 includes three (3) interface connection ports 1204, however, the monitor may include any number of such ports 1204.

With the access panel 1202 removed, electrical devices having, for example, wires may be electrically and communicatively coupled to the appropriate input/output connectors inside the monitor 100 (e.g., interior cavity 1302 shown in FIG. 13). The access panel also allows access the electrical components (integrated circuits such as processing circuit, memory circuit, etc. or other electrical components) within the interior cavity 1302. Such access may be needed for servicing of the monitor 100. According to one embodiment, the access panel 1202 may also serve as a heat sink to dissipate heat generated by the internal circuitry of the monitor 100. The access panel 1202 may be secured in place with screws 1208 and forms a water-resistant seal. According to one embodiment, the access panel 1202 may include fins and is configured to dissipate heat generated by the internal circuitry of the display monitor 100.

With the peripheral device interface connector covers 1206 removed, an operator may access the peripheral device interface connectors 1304. The peripheral device interface connectors 1304 allow the display monitor 100 to electrically and communicatively couple to a variety of different electronic devices such as, but not limited to, digital cameras, digital video cameras, microphones, wireless communication devices, speakers, wireless video input, a sensor, motion detectors, light detectors, digital music players, etc. The interface connectors 1304 may also be any type of electrical communication connection including, but not limited to, universal serial bus (USB) ports, proprietary ports, digital video input, other display ports, HDBaseT® ports, etc. The interface connectors 1304 may mate with corresponding connectors located on the peripheral electronic devices (not shown) in such a fashion so as to form a liquid-resistant seal to prevent liquid and moisture from penetrating the interface connection at the interface connector 1304. The peripheral device interface connector ports 1204 may also be liquid-resistant in that they prevent liquid from entering the internal cavity 1302 of the monitor 100 and/or the interface connectors 1304. The interface connector covers 1206 may be secured in place with screws 1210 and form water-resistant seals.

Figure 14:
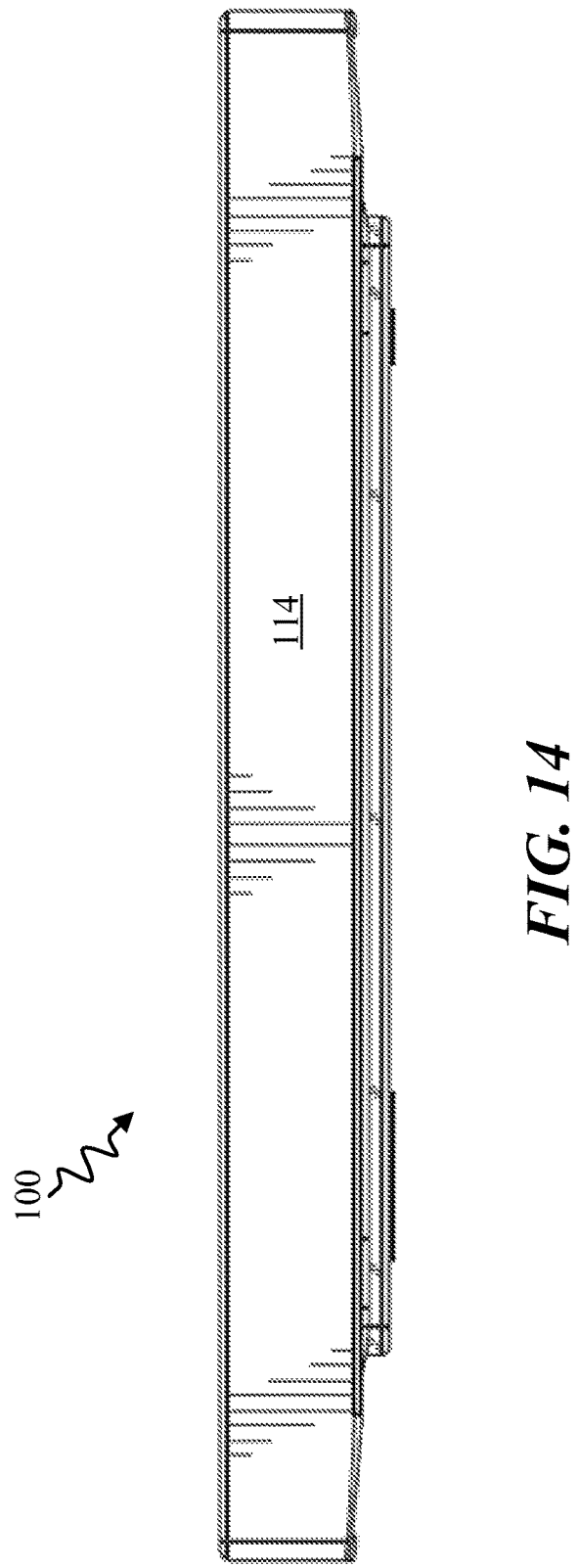
FIG. 14 illustrates a top view of the display monitor.

FIG. 14 illustrates a top view of the display monitor 100.

Figure 15:
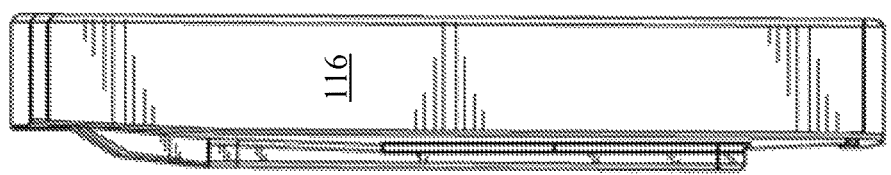
FIG. 15 illustrates a side view of the display monitor.

FIG. 15 illustrates a side view of the display monitor 100.

One or more of the components and functions illustrated in the drawings may be rearranged and/or combined into a single component or embodied in several components without departing from the invention. Additional elements or components may also be added without departing from the invention. While certain exemplary embodiments have been described and shown in the accompanying drawings, it is to be understood that such embodiments are merely illustrative of and not restrictive of the present disclosure, and that the present disclosure should not be limited to the specific constructions and arrangements shown and described, since various other modifications are possible. Therefore, it is to be understood that, within the scope of the appended claims, embodiments of the present disclosure may be practiced other than as specifically described herein.

What is claimed is:

1. A display monitor comprising:
a display having a front side surface that, at least a portion of, displays images;
a frame housing the display, the frame including at least one perimeter edge surface that extends along a perimeter of the display, the frame further including a front side surface that extends about a perimeter of the frame and is substantially orthogonal to the perimeter edge surface;
a space between the front side surface of the frame and the front side surface of the display that extends around the perimeter of the display; and
a protective overmolding that removeably couples to and encases the perimeter edge surface and the front side surface of the frame, the overmolding including a lip that extends about the perimeter of the frame and resides within the space to form a liquid-resistant seal between the front side surfaces of the display and the frame, the overmolding being at least one of an elastic material, rubber, or silicone.

2. The display monitor of claim 1, wherein the frame further includes a back side surface that extends about the perimeter of the frame and is substantially orthogonal to the perimeter edge surface, and the protective overmolding removeably couples to and encases at least a portion of the back side surface of the frame.

3. The display monitor of claim 2, wherein the back side surface includes a groove that extends about the perimeter of the frame, and the protective overmolding removeably couples to and encases the groove.

4. The display monitor of claim 3, wherein the groove includes a well and the overmolding includes a notch that couples to and resides within the well.

5. The display monitor of claim 1, wherein the perimeter edge surface includes a first perimeter edge surface, a second perimeter edge surface, a third perimeter edge surface, and a fourth perimeter edge surface, the first and third perimeter edge surfaces parallel to each other, the second and fourth perimeter edge surfaces parallel to each other, and the first and third perimeter edge surfaces orthogonal to the second and fourth perimeter edge surfaces.

6. The display monitor of claim 5, wherein a thickness of the third perimeter edge surface is at least 50% thicker than thicknesses of each of the first, second, and fourth perimeter edge surfaces.

7. The display monitor of claim 1, wherein the frame further includes a back side surface having at least one peripheral device interface connection port, the interface connection port including an interface connector.

8. The display monitor of claim 7, wherein the interface connection port further includes an interface connector cover removeably coupled to the back side surface of the frame and configured to cover the interface connector, the interface connector cover further configured to prevent moisture from entering at least one of an interior cavity of the display monitor or the interface connector.

9. The display monitor of claim 7, wherein the back side surface of the frame further has at least one access panel configured to allow access to an interior cavity of the display monitor, the access panel removeably coupled to the back side surface of the frame.

10. The display monitor of claim 9, wherein the access panel includes fins and is configured to dissipate heat generated by the display monitor.

11. A display monitor comprising:
means for displaying images having a front side surface;
means for housing the means for displaying images, the means for housing including at least one perimeter edge surface that extends about a perimeter of the means for housing, the means for housing further including a front side surface that extends about a perimeter of the means for housing and is substantially orthogonal to the perimeter edge surface;
a space between the front side surface of the means for housing and the front side surface of the means for displaying that extends around the perimeter of the means for displaying; and
means for protecting the display monitor, the means for protecting coupling to and encasing the perimeter edge surface and the front side surface of the means for housing, the means for protecting including a lip that extends about the perimeter of the means for housing and resides within the space to form a liquid-resistant seal between the front side surfaces of the means for displaying and the means for housing, the means for protecting including at least one of an elastic material, rubber, or silicone.

12. The display monitor of claim 11, wherein the means for housing further includes a back side surface that extends about the perimeter of the means for housing and is substantially orthogonal to the perimeter edge surface, and the means for protecting removeably couples to and encases at least a portion of the back side surface of the means for housing.

13. The display monitor of claim 12, wherein the back side surface includes a well that extends about the perimeter of the means for housing and the means for protecting includes a notch that couples to and resides within the well.

14. The display monitor of claim 11, wherein the means for housing further includes a back side surface having at least one peripheral device interface connection port, the interface connection port including an interface connector and an interface connector cover removeably coupled to the back side surface of the frame, the interface connector cover configured to cover the interface connector and prevent moisture from entering at least one of an interior cavity of the display monitor or the interface connector.

15. A display monitor comprising:
a display having a front side surface that, at least a portion of, displays images;
a frame housing the display, the frame including at least four perimeter edge surfaces that extend along a perimeter of the frame, the frame further including a front side surface that extends about a perimeter of the frame and is substantially orthogonal to the perimeter edge surfaces;
an overmolding that couples to the perimeter edge surfaces and the front side surface of the frame, the overmolding extending about the perimeter of the frame and including a means for sealing that resides within a space between the front side surface of the display and the frame and the means for sealing is configured to prevent liquid from entering an internal cavity of the display monitor through the space.

16. The display monitor of claim 15, wherein the overmolding is made of, at least in part, at least one of rubber and/or silicone.

* * * * *